United States Patent [19]

Edwards

[11] 4,208,400
[45] Jun. 17, 1980

[54] ASSAY OF OESTROGEN

[75] Inventor: John C. Edwards, Amersham, England

[73] Assignee: The Radiochemical Centre Limited, Buckinghamshire, England

[21] Appl. No.: 908,238

[22] Filed: May 22, 1978

[30] Foreign Application Priority Data

May 24, 1977 [GB] United Kingdom ............... 21870/77

[51] Int. Cl.$^2$ ...................... G01N 33/16; A61K 43/00
[52] U.S. Cl. ..................................... 424/1; 23/230 B; 424/12
[58] Field of Search ..................... 424/1, 12; 73/230 B

[56] References Cited

U.S. PATENT DOCUMENTS 4,081,525  3/1978  Knight et al. ............................. 424/1

OTHER PUBLICATIONS

Crosignani et al., Radioimmunoassay of Steroid Hormones, Ed. Gupta, Verlag Chemie, Weinheim, 1975, pp. 105-115.

Davis et al., J. Clin. Endo. Met, vol. 40, No. 5, May 1975, pp. 895-899.

Schiller et al., Clin. Chem., vol. 22, No. 3, Mar. 1976, pp. 359-363.

Edwards et al., Chemical Abstracts, vol. 85, No. 17, Oct. 25, 1976, p. 267, Abstract No. 119237c.

*Primary Examiner*—Richard E. Schafer
*Assistant Examiner*—Christine M. Nucker
*Attorney, Agent, or Firm*—Wenderoth, Lind & Ponack

[57] ABSTRACT

A method for assaying unconjugated oestriol in serum by radioimmunoassay is characterized by incorporating progesterone in the incubated assay mixture in an amount to substantially reduce the effect of non-specific steroid-binding proteins present in the serum.

6 Claims, No Drawings

ASSAY OF OESTROGEN

The invention relates to the novel use of a steroid to block the action of steroid-binding proteins in pregnancy serum and plasma samples, thereby minimizing interference in a direct radioimmunoassay for unconjugated oestriol using a specific anti-oestriol serum.

Oestriol exists in serum and plasma as a mixture of the unconjugated form together with a number of conjugates of oestriol present as glucuronides and sulphates. The unconjugated form is only about 10% of the total amount of oestriol including the conjugates.

It has not previously been possible to measure unconjugated oestriol directly in serum or plasma samples by radioimmunoassay procedures because antisera produced against oestriol usually cross-react with some of the conjugates of oestriol. The cross-reaction of oestriol-3-sulphate, for example, is 10–30% compared with oestriol, and the circulating levels of this conjugate are twice as high as unconjugated oestriol.

Because the presently-used antisera cannot distinguish between oestriol and some of the oestriol conjugates, the only known radioimmunoassays for unconjugated oestriol involve extraction of oestriol from the serum or plasma samples using an organic solvent, removal of the organic solvent by evaporation and redissolving the oestriol in a suitable buffered solution for determination by radioimmunoassay.

We have found that by careful screening of antisera produced by immunizing rabbits with oestriol conjugated to bovine serum albumin, it is possible to find a specific antiserum to oestriol which does not cross-react significantly with oestriol conjugates, and which allows the direct radioimmunoassay of unconjugated oestriol in serum or plasma samples. The assay is performed by pipetting into plastic tubes 20 μl of sample or standard, 200 μl of a buffered solution of $^{125}$I-labelled oestriol and 200 μl of a dilution of the specific anti-oestriol serum in a buffered solution. After mixing, the tubes are allowed to stand for 60 minutes at ambient temperature. 500 μl of an ammonium sulphate solution is then added to each tube and the contents thoroughly mixed. After centrifugation, the supernatant liquids are removed and the radioactivity in the precipitates is measured. Standard solutions of oestriol in male serum are used to construct a dose-response curve, and unknown samples are interpolated from the curve.

A particular problem with the direct radioimmunoassay of unconjugated oestriol in pregnancy is caused by the increased amount of steroid-binding proteins present in pregnancy serum and plasma. The steroid-binding proteins react with oestriol and $^{125}$I-labelled oestriol during the assay procedure, and the steroid-protein bound $^{125}$I-labelled oestriol is precipitated along with the antibody-bound $^{125}$I-labelled oestriol by the ammonium sulphate solution separation system. The male serum standards do not contain abnormally high levels of steroid-binding proteins. Consequently the direct assay of oestriol in pregnancy serum or plasma samples will result in higher radioactivity in the precipitated "bound" fraction (due to the additional binding protein) than in the standard oestriol solutions in male serum.

The effect of the steroid-binding proteins in the assay system is best observed by measuring "blank" values of pregnancy samples and comparing them with "blank" values of male serum. The "blank" value of the sample is the percent of total radioactivity found in the precipitate in the absence of antiserum. That is, in the assay system described above, the buffered solution of antiserum is replaced by buffer alone.

Pooled male sera blank = 9.0%
Pooled pregnancy sera blank = 13.7%

This invention arises from the discovery that the effect of the binding protein in the pregnancy samples may be reduced by the addition of progesterone which reacts with the binding protein but has low cross-reaction with the anti-serum.

According to the invention, there is provided, in a method of performing a competitive immunoassay for unconjugated oestriol by (a) providing a mixture of a standard amount of oestriol-containing sample to be assayed, a standard amount of a labelled version of oestriol, and a standard amount, insufficient to react with all the unconjugated oestriol and labelled oestriol present, of an antibody to oestriol, (b) incubating the mixture, whereby a part of the free unconjugated oestriol and a part of the labelled oestriol, the proportion depending on the initial concentrations of unconjugated oestriol and labelled oestriol present, become bound to the antibody, (c) separating the part of the unconjugated and the labelled oestriol bound to the antibody from the part not so bound, and measuring the concentration of the bound labelled oestriol and/or the unbound labelled oestriol, the improvement which consists in providing in the initial mixture progesterone in an amount large enough to react with the major part of any steriod-binding proteins present in the sample to be assayed but not so large as to react with more than a minor part of the antibody to oestriol, whereby nearly all unconjugated oestriol present in the initial mixture is available for reaction with the oestriol antibody, and nearly all the oestriol antibody present in the initial mixture is available for reaction with unconjugated and labelled oestriol.

The labelled version of oestriol is preferably radioactively labelled, and may advantageously be the (iodine-125) 2-iodo, 4-iodo or 2,4-di-iodo derivative of oestriol described in our German OS No. 2600465.9.

Preferably, the progesterone is present in an amount to reduce the effect of the non-specific steroid-binding proteins by at least 75%, but to reduce the effect of the oestriol antibody by not more than 10%. We have found that a progesterone concentration in the range 1 μg to 20 μg per ml. of unknown serum is generally appropriate. Where the serum is diluted by a factor of about 20, as in the assay described herein, it may be more convenient to calculate the progesterone concentration as from 0.05 μg to 1.0 μg per ml. of the incubated assay solution.

In the following Example, the progesterone was conveniently added to the assay system by being included (in the concentrations indicated) in the buffered solution of $^{125}$I-labelled oestriol.

| Concentration added (μg/ml) | Male serum blank | Pregnancy serum blank | Co |
| --- | --- | --- | --- |
| 0 | 9.0 | 13.8 | 67.6 |
| 0.009 | 8.8 | 13.4 | 67.1 |
| 0.09 | 9.0 | 11.5 | 66.9 |
| 0.9 | 8.8 | 10.0 | 66.6 |
| 9.0 | 8.5 | 10.3 | 62.3 |

(Co is the percent total radioactivity found in the precipitate in the radioimmunoassay system in the absence of oestriol.)

Progesterone reduced the difference between the blank values of male serum and pregnancy serum from 4.8% to 1%. This difference was then thought to be negligible in the assay system. The steroid showed a very slight reaction with the antiserum at high steroid concentrations, as seen by the fall in Co values. A concentration of 0.4 μg progesterone per ml. of buffered solution of the labelled oestriol, that is to say, about 0.2 μg progesterone per ml. of the incubated assay solution, was chosen as the lowest concentration which effectively blocked the action of the binding proteins, and which could therefore be used in an assay system for oestriol.

EXAMPLE 1

Radioimmunoassay of unconjugated oestriol

Samples of 20 μl of standard solutions of oestriol in male human serum, or of the unknown pregnancy serum samples, are pipetted into plastic tubes. To each tube is added 200 μl of phosphate buffer containing 10% horse serum, sodium azide (1 mg/ml), gelatine (1 mg/ml), progesterone (0.4 μg/ml) and a $^{125}$I-labelled oestriol derivative (approximately 0.3 μCi/ml). After mixing, 200 μl of the phosphate buffer containing horse serum, sodium azide and gelatine, and containing a dilution of a specially selected antiserum produced against oestriol conjugated to albumin is added to each tube. The contents of the tubes are again mixed, and then the tubes are left at ambient temperature for 60 minutes, 500 μl of an ammonium sulphate solution (35% w/v in water) is then added to each tube and, after mixing, the tubes are centrifuged. The supernatant liquids are then removed by aspiration and the radioactivity of the precipitates in the tubes are measured in a gamma-counter.

RESULTS

| Oestriol standard (ng/ml) | Counts in 100 sec. |
| --- | --- |
| 0 | 96196 |
| 0 | 96318 |
| 1.25 | 65612 |
| 1.25 | 65545 |
| 5.3 | 37322 |
| 5.3 | 37457 |
| 12.5 | 25818 |
| 12.5 | 25736 |
| 29.0 | 19791 |
| 29.0 | 18136 |

What we claim is:
1. In a method of performing a competitive immunoassay for unconjugated oestriol by
   (a) providing a mixture of a standard amount of oestriol-containing sample to be assayed, a standard amount of a labelled version of oestriol, and a standard amount, insufficient to react with all the unconjugated oestriol and labelled oestriol present, of an antibody to oestriol,
   (b) incubating the mixture, whereby a part of the unconjugated oestriol and a part of the labelled oestriol, the proportion depending on the initial concentrations of unconjugated oestriol and labelled oestriol present, become bound to the antibody,
   (c) separating the part of the unconjugated and the labelled oestriol bound to the antibody from the part not so bound, and measuring the concentration of the bound labelled oestriol and/or the unbound labelled oestriol,
   the improvement which consists in providing in the initial mixture progesterone in an amount large enough to react with the major part of any steriod-binding proteins present in the sample to be assayed but not so large as to react with more than a minor part of the antibody to oestriol, whereby nearly all unconjugated oestriol present in the initial mixture is available for reaction with the oestriol antibody, and nearly all the oestriol antibody present in the initial mixture is available for reaction with unconjugated and labelled oestriol.

2. A method as claimed in claim 1, wherein the labelled version of oestriol is radioactively labelled.

3. A method as claimed in claim 2, wherein the radioactively labelled oestriol is the (iodine-125) 2-iodo, 4-iodo or 2,4-di-iodo derivative of oestriol.

4. A method as claimed in any one of claims 1 to 3, wherein the progesterone concentration is from 0.05 μg to 1.0 μg per ml. of the incubated mixture.

5. A method as claimed in any one of claims 1 to 3, wherein the sample to be assayed is a sample of serum, and the progesterone concentration is from 1 μg to 20 μg per ml. of the sample of serum.

6. A method as claimed in any one of claims 1 to 3, wherein the antibody to oestriol is one which does not cross-react significantly with oestriol conjugates.

* * * * *